US00PP15250P2

(12) United States Plant Patent
Larsen

(10) Patent No.: US PP15,250 P2
(45) Date of Patent: Oct. 19, 2004

(54) ***OSTEOSPERMUM* PLANT NAMED 'SUNNY FLORA'**

(50) Latin Name: *Osteospermum ecklonis*
Varietal Denomination: Sunny Flora

(76) Inventor: Bjarne Nyholm Larsen, Grönnegyden 148, DK-5270 Odense N (DK)

( * ) Notice: Subject to any disclaimer, the term of this patent is extended or adjusted under 35 U.S.C. 154(b) by 0 days.

(21) Appl. No.: 10/743,064

(22) Filed: Dec. 22, 2003

(51) Int. Cl.[7] ..... A01H 5/00
(52) U.S. Cl. ..... Plt./360
(58) Field of Search ..... Plt./360

(56) References Cited

PUBLICATIONS

UPOV–ROM GTITM, Plant Variety Database, 2004/01, GTI jouve Retrieval Software, Citation for *Osteospermum* 'Sunny Flora'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Osteospermum* plant named 'Sunny Flora', characterized by its compact, upright and mounded plant habit; dense and bushy growth habit; freely flowering habit; and red purple-colored ray florets and dark purple-tipped disc florets.

2 Drawing Sheets

Botanical classification/cultivar designation: *Osteospermum ecklonis* cultivar Sunny Flora.

BACKGROUND OF THE INVENTION

The present Invention relates to a new and distinct cultivar of *Osteospermum* plant, botanically known as *Osteospermum ecklonis,* and hereinafter referred to by the name 'Sunny Flora'.

The new Petunia is a product of a planned breeding program conducted by the Inventor in Odense, Denmark. The objective of the breeding program is to create new compact *Osteospermums* with continuous flowering, good postproduction longevity and attractive flower coloration.

The new *Osteospermum* originated from a self-pollination made by the Inventor in 2001 of the *Osteospermum ecklonis* cultivar Sunny Alex, not patented.

The new *Osteospermum* was discovered and selected by the Inventor as a single flowering plant within the resulting progeny from the self-pollination in a controlled environment in Odense, Denmark.

Asexual reproduction of the new *Osteospermum* by terminal vegetative cuttings was first conducted in Odense, Denmark. Asexual reproduction by cuttings has shown that the unique features of this new *Osteospermum* are stable and reproduced true to type in successive generations.

SUMMARY OF THE INVENTION

The cultivar Sunny Flora has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sunny Flora'. These characteristics in combination distinguish 'Sunny Flora' as a new and distinct *Osteospermum:*

1. Compact, upright and mounded plant habit.
2. Dense and bushy growth habit.

3. Freely flowering habit.
4. Large inflorescences.
5. Red purple-colored ray florets and dark purple-tipped disc florets.

Compared to plants of the parent, the cultivar Sunny Alex, plants of the new *Osteospermum* are more compact, have lighter green-colored leaves, and have shorter and stronger peduncles.

Plants of the new *Osteospermum* can be compared to plants of the cultivar Sunny Lady, disclosed in U.S. Plant Pat. No. 10,353. In side-by-side comparisons conducted in Fyn, Denmark, plants of the new *Osteospermum* differed from plants of the cultivar Sunny Lady in the following characteristics:

1. Plants of the new *Osteospermum* were more compact and denser than plants of the cultivar Sunny Lady.
2. Plants of the new *Osteospermum* were more upright and not as outwardly spreading as plants of the cultivar Sunny Lady.
3. Plants of the new *Osteospermum* had lighter green-colored foliage than plants of the cultivar Sunny Lady.
4. Plants of the new *Osteospermum* and the cultivar Sunny Lady differed in ray floret coloration as plants of the cultivar Sunny Lady had lighter-colored ray florets.
5. Plants of the new *Osteospermum* had longer and sturdier peduncles than plants of the cultivar Sunny Lady.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph on the first sheet comprises a side perspective view of a typical flowering plant of 'Sunny Flora' grown in a 11-cm container.

The photograph on the second sheet is a top perspective view of a typical flowering plant of 'Sunny Flora'.

DETAILED BOTANICAL DESCRIPTION

The aforementioned photographs and following observations and measurements describe plants grown in Fyn, Denmark, in a glass-covered greenhouse during the winter and spring. After planting rooted cuttings, plants were grown for about 20 weeks in 11-cm containers. During the first five weeks of production of the plants, day and night temperatures were about 20° C., then temperatures were reduced to 14° C. Color references were made to The Royal Horticultural Society Colour Chart, 4$^{th}$ Edition, except where general terms of ordinary dictionary significance are used.

Botanical Classification: *Osteospermum ecklonis* cultivar Sunny Flora.

Parentage: Self-pollination of *Osteospermum ecklonis* cultivar Sunny Alex, not patented.

Propagation:

*Type.*—Terminal vegetative cuttings.

*Time to initiate rooting.*—About 10 to 14 days at 18 to 21° C.

*Root description.*—Fine, fibrous and branching.

Plant description:

*Appearance.*—Perennial herbaceous container and garden plant. Compact, upright and mounded plant habit. Freely branching; dense and bushy growth habit. Vigorous growth rate.

*Plant height.*—About 17 cm.

*Plant width or area of spread.*—About 17 cm.

*Lateral branches.*—Quantity per plant: About four primary lateral branches and about seven secondary lateral branches. Length, primary branches: About 3 cm. Length, secondary branches: About 7 to 12 cm. Diameter, primary and secondary branches: About 4 to 5 mm. Internode length: About 3 mm. Aspect: Mostly upright to about 10 to 20° from vertical. Strength: Strong, sturdy. Texture: Smooth, glabrous. Color: 144C.

*Foliage description.*—Arrangement: Alternate; simple. Length: About 3 to 5 cm. Width: About 1 to 4 cm. Shape: Obovate to lanceolate. Apex: Obtuse. Base: Attenuate. Margin: Broadly serrate. Venation pattern: Pinnate. Texture, upper and lower surfaces: Pubescent; scattered short, stiff hairs. Color: Developing foliage, upper surface: 147A. Developing foliage, lower surface: 148C. Fully expanded foliage, upper surface: 139B; venation, same as lamina. Fully expanded foliage, lower surface: 147A; venation, 148B. Petiole: Length: About 1 to 2 cm. Diameter: About 2 to 4 mm. Texture, upper and lower surfaces: Smooth. Color, upper and lower surfaces: 145B.

Inflorescence description:

*Appearance.*—Terminal and axillary inflorescences held above and beyond the foliage on moderately strong and sturdy peduncles. Composite inflorescence form, radially symmetrical, with elliptic-shaped ray florets and disc florets massed at the center; ray and disc florets develop acropetally on a capitulum. Inflorescences persistent. Inflorescences face mostly upright to about 10° from vertical.

*Flowering response.*—Plants flower continuous and freely from the spring through the fall.

*Postproduction longevity.*—Inflorescences maintain good color and substance for about five to ten days on the plant.

*Quantity of inflorescences per plant.*—Freely flowering; about 15 buds and open inflorescences.

*Fragrance.*—Faint; fresh, lemon-like.

*Inflorescence diameter.*—About 6 to 7 cm.

*Disc diameter.*—About 1.5 cm.

*Inflorescence buds.*—Length: About 1.2 cm. Diameter: About 1 cm. Shape: Globular. Color: Towards the base, 145C; towards the apex, 154B.

*Ray florets.*—Length: About 2.5 to 2.8 cm. Width: About 8 mm. Shape: Elliptic. Apex: Rounded with slight emargination. Base: Acute. Margin: Entire. Texture, upper and lower surfaces: Smooth, satiny. Orientation: Initially upright then about 80° from vertical. Number of ray florets per inflorescence: About 18 in one whorl. Color: When opening, upper surface: Ground color, 75C; towards the apex, 77B. When opening, lower surface: Ground color, 155D, with longitudinal stripes, 94B. Fully opened, upper surface: Ground color, 72A; towards the base, 75D. Fully opened, lower surface: Ground color, 91A, with longitudinal stripes, 90A.

*Disc florets.*—Shape: Tubular, elongated. Apex: Five-pointed. Length: About 6 mm. Width: At apex, about 2 mm; at base, about 1 mm. Number of disc florets per inflorescence: About 50. Color, immature: 90B. Color, mature: N155B tipped with N89B.

*Phyllaries.*—Quantity per inflorescence: About 15. Length: About 6 to 12 mm. Width: About 1 to 3 mm. Shape: Lanceolate. Apex: Acuminate. Base: Fused. Margin: Entire. Color: 137D.

*Peduncles.*—Length: About 5 to 7 cm. Diameter: About 2 mm. Strength: Moderately strong; sturdy. Texture: Smooth. Color: 144C.

*Reproductive organs.*—Androecium: Stamen number: Five per floret; fused around style. Anther shape: Linear. Anther length: About 2 mm. Anther color: N99B. Pollen amount: Abundant. Pollen color: N25B. Gynoecium: Pistil number: One per floret. Pistil length: About 4 mm. Pistil color: N187A. Style length: About 2 mm. Stigma shape: Two-parted. Stigma color: N187A. Ovary color: 2D.

*Seed.*—Length: About 2 to 3 mm. Diameter: About 1 mm.

Disease/pest resistance: Resistance to pathogens and pests common to *Osteospermums* has not been observed on plants grown under commercial greenhouse or outdoor conditions.

Weather tolerance: Plant of the new *Osteospermum* have been observed to tolerate drought, rain, wind, and temperatures from about 1 to 35° C.

It is claimed:

1. A new and distinct cultivar of *Osteospermum* plant named 'Sunny Flora', as illustrated and described.

* * * * *

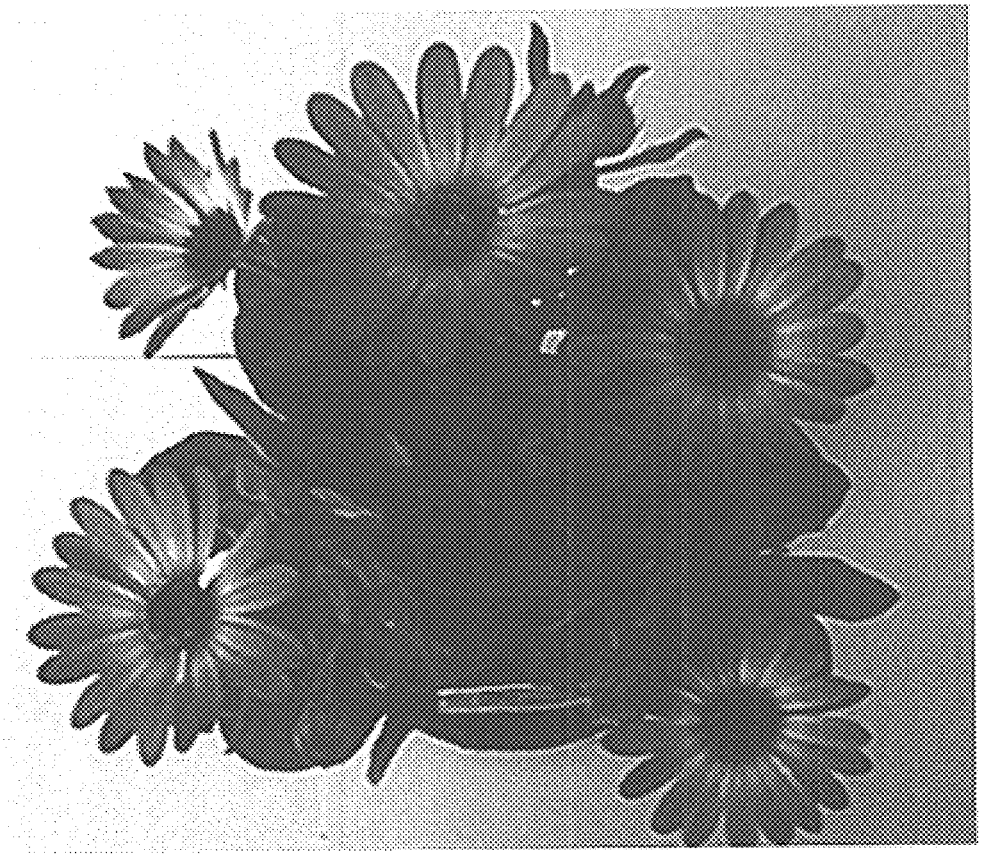

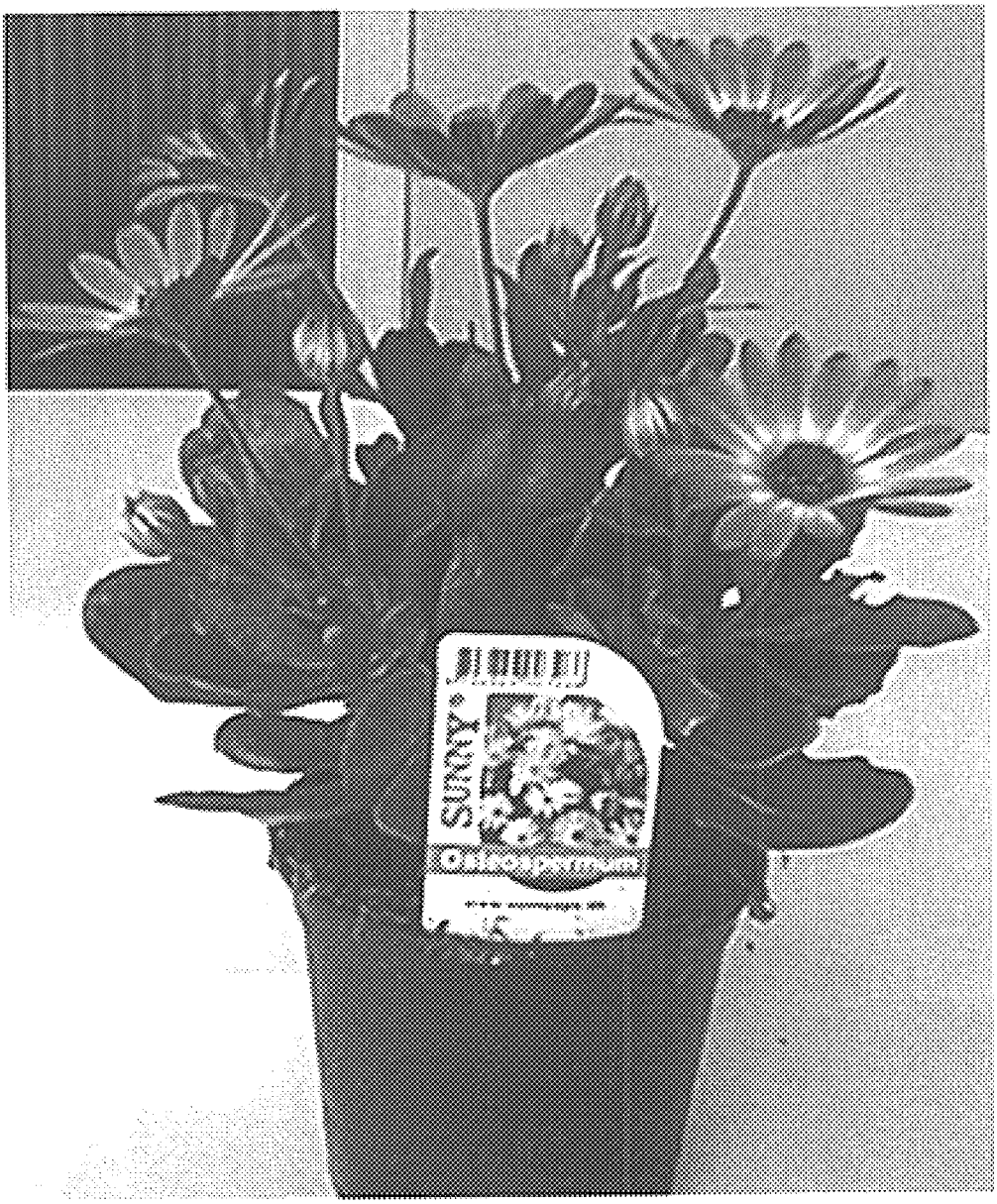
SUNNY
Osteospermum